United States Patent
Punsch et al.

(10) Patent No.: US 10,952,955 B2
(45) Date of Patent: Mar. 23, 2021

(54) COMPOSITION TO REDUCE THE DRYING TIME OF KERATIN FIBERS, METHOD AND USE THEREOF

(71) Applicant: KAO GERMANY GMBH, Darmstadt (DE)

(72) Inventors: Britta Punsch, Darmstadt (DE); Sabine Schmid, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 209 days.

(21) Appl. No.: 15/277,531

(22) Filed: Sep. 27, 2016

(65) Prior Publication Data
US 2018/0028433 A1    Feb. 1, 2018

(30) Foreign Application Priority Data

Jul. 26, 2016 (EP) .................................... 16181290

(51) Int. Cl.
| | | |
|---|---|---|
| *A61Q 5/00* | (2006.01) | |
| *A61K 8/898* | (2006.01) | |
| *A61Q 5/12* | (2006.01) | |
| *A61K 8/81* | (2006.01) | |
| *A45D 7/00* | (2006.01) | |
| *A45D 20/04* | (2006.01) | |
| *A61Q 5/06* | (2006.01) | |

(52) U.S. Cl.
CPC .............. *A61K 8/898* (2013.01); *A61K 8/817* (2013.01); *A61K 8/8152* (2013.01); *A61K 8/8182* (2013.01); *A61Q 5/00* (2013.01); *A61Q 5/12* (2013.01); *A45D 20/04* (2013.01); *A45D 2007/008* (2013.01); *A61K 2800/432* (2013.01); *A61K 2800/594* (2013.01); *A61Q 5/065* (2013.01)

(58) Field of Classification Search
None
See application file for complete search history.

(56) References Cited

U.S. PATENT DOCUMENTS

| | | | | |
|---|---|---|---|---|
| 2009/0226381 A1* | 9/2009 | Maillefer | ............... | A61K 8/898 424/47 |
| 2012/0064137 A1* | 3/2012 | Kawai | .................... | A61K 8/817 424/401 |
| 2014/0328787 A1* | 11/2014 | Mette | ..................... | A61K 8/41 424/70.21 |

FOREIGN PATENT DOCUMENTS

| | | | |
|---|---|---|---|
| DE | 102014221400 | * | 4/2016 |
| WO | 2014071354 A1 | | 5/2014 |

OTHER PUBLICATIONS

Translated DE 102014221400 (Apr. 2016).*
Database GNPD [Online], Mintel; Sep. 24, 2014; anonymous: "Shampoo", XP055620371, retrieved form www.gnpd.com Database accession No. 2682153.
"Speed-Dry Styling Spray", GNPD, XP002741105, [retrieved on Jan. 1, 2007].
Database GNPD [Online] Mintel; Feb. 22, 2012, anonymous: "Frizz Control & Straghtening Conditioner", XP055620140, retrieved from www.gnpd.com DATAbase accession No. 1732879.

* cited by examiner

*Primary Examiner* — Jyothsna A Venkat
(74) *Attorney, Agent, or Firm* — Norris McLaughlin, P.A.

(57) ABSTRACT

The present invention is on the provision of a composition, method, use of composition to reduce the drying time of keratin fibers, preferably human hair. The composition is aqueous and comprises two or more cationic polymers wherein one of the cationic polymers has a charge density in the range of 2 meq/g to 4 meq/g, and the other cationic polymer has a charge density in the range of 4.1 meq/g to 7 meq/g, and an aminosilicone. A kit of parts is disclosed which comprises the composition and a blow dryer.

9 Claims, No Drawings

COMPOSITION TO REDUCE THE DRYING TIME OF KERATIN FIBERS, METHOD AND USE THEREOF

BACKGROUND OF THE INVENTION

The present invention is on a composition, a method, a use, and kit-of-parts to reduce the drying time of wet or moist keratin fibers, preferably human keratin fibers, and more preferably human hair.

A common method to reduce the drying time of hair is raising the temperature of the hair combined with a steady airflow to allow for faster drying. Especially for customers with long hair, the drying time upon cleansing and/or styling is a significant factor and commonly shortened by heating the hair by means such as a blow-dryer.

Nevertheless, blow-drying is time consuming as well and due to the heat exposure to hair is conferred a non-negligible amount of heat damage.

As for the heat damage, cationic conditioning polymers with a charge density between 4.1 meq/g and 7 meq/g are commonly employed as conditioning polymers in hair science (WO2014071354, IP.com 000242076D). Such polymers having a cationic charge density from 4.1 meq/g and 7 meq/g are also marketed for relaxing curly/kinky hair (Mintel 10107510).

However, as time is a costly good across all industry sectors and for individual customers as well, a reduction of process times while maintaining an at least equal amount of service quality is strongly encouraged by everyone. Therefore it would be highly desirable for efficiency reasons to reduce the time of heat exposure to hair while maintaining its healthy state.

It has been found out that the combination of two cationic polymers with certain charge densities and an aminosilicone reduces the drying time of hair. With respect to prior art, the literature is silent on the core of the present invention.

SUMMARY OF THE INVENTION

Therefore, the first object of the present invention is an aqueous cosmetic composition for keratin fibers, preferably human hair, characterized in that it comprises two or more cationic polymers and/or their salts wherein one cationic polymer has a charge density in the range of 2 meq/g to 4 meq/g, and the other cationic polymer has a charge density in the range of 4.1 meq/g to 7 meq/g, wherein the composition comprises an aminosilicone.

The second object of the present invention is the use of the composition as defined above for reducing the drying time of wet hair.

The third object of the present invention is a method for reducing the drying time of hair wherein the composition as defined above is applied onto hair before or after washing the hair, and the hair is dried with a hair drier.

The fourth object of the present invention is a kit of parts comprising the composition as defined above and at least one blow drier.

DETAILED DESCRIPTION OF THE INVENTION

The cationic charge density according to the present invention is calculated as the number of cationic charges per unit divided by molecular weight of the unit and multiplied by 1000 in order to express it as meq/g. It is to be noted that the reported charge density values in the following sections are to be understood as rounded values to one digit instead of exact numbers.

The composition comprises at least one cationic polymer having a cationic charge density from 2.0 meq/g to 4.0 meq/g.

Polymers having a cationic charge density from 2 meq/g to 4 meq/g are selected from:

(1) polymers known under the CTFA name Polyquaternium 16 and/or its salts which are marketed as Luviquat FC 370, Luviquat FC 550, and Luviquat HM 552 having a cationic charge density of 2.0 meq/g, 3.3 meq/g, and 3.0 meq/g, respectively.

(2) polymer known under the CTFA name Polyquaternium 7 and/or its salts which is available with the trade name Merquat 550 having a charge density of 3.1 meq/g.

The preferred cationic polymer with a cationic charge density from 2 meq/g to 4 meq/g is Polyquaternium 16.

The total concentration of the polymers having a charge density from 2 meq/g to 4 meq/g comprised in the composition ranges from 0.01% to 10% by weight, more preferably from 0.1% to 5% by weight, further more preferably from 0.2% to 4% by weight, and most preferably from 0.5% to 3% by weight, calculated to the total of the composition.

The composition of the present invention comprises at least one cationic polymer with a charge density from 4.1 meq/g to 7 meq/g. Suitable cationic polymers are selected from:

(1) polymers known under the CTFA name Polyquaternium 22 and/or its salts which are sold under the trade name Merquat 295 having a cationic charge density of 6.0 meq/g, and Merquat 280 having a cationic charge density of 5.0 meq/g.

(2) polymers known under the CTFA name Polyquaternium 16 and/or its salts which are marketed as Luviquat Excellence having a cationic charge density of 6.1 meq/g.

(3) polymers known under the CTFA name Polymethacrylamidopropyltrimonium chloride and sold under the tradename N-Durhance A-1000 while having a cationic charge density of 4.8 meq/g.

(4) polymers sold under the CTFA name Polyquaternium 37 and/or its salts offered as Ultragel 300 having a charge density of 5.8 meq/g.

The preferred cationic polymer with a charge density of 4.1 meq/g to 7 meq/g is Polyacrylamidopropyltrimonium chloride.

The composition comprises cationic polymers with a charge density of 4.1 meq/g to 7 meq/g at a concentration from 0.01% to 5% by weight, preferably from 0.05% to 2% by weight, and more preferably from 0.1% to 1% by weight, calculated to the total of the composition.

The weight ratio of the total cationic polymers having cationic charge density in the range of 2.0 to 4.0 meq/g to the total cationic polymers having cationic charge density in the range of 4.1 to 7.0 meq/g is in the range of 5:1 to 1:1, preferably 3:1 to 1:1.

The composition comprises an aminosilicone wherein the term aminosilicone is to be understood as an aminated silicone comprising at least one primary, secondary, tertiary, or quaternary amino group and is referred to as amodimethicone or aminodimethicone. The aminosilicone is selected from:

(1) a compound according to the general structure

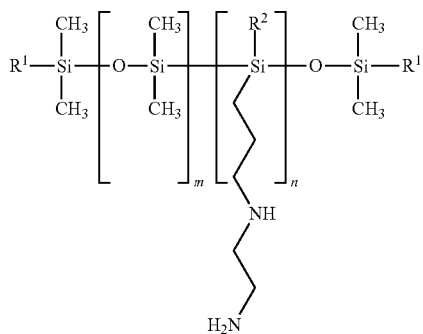

Wherein $R^1$ is selected from OH, $OCH_3$, and/or $O-Si-(CH_3)_3$, $R^2$ is selected from $CH_3$, $OCH_3$, $O-(Si-(CH_3)_2)_x-R^1$, and/or $O-Si-(CH_3)_3$, with the provision that if $R^1$ or $R^2$ are selected from $O-Si-(CH_3)_3$, then all other $R^1$ or $R^2$ are selected from $O-Si-(CH_3)_3$ and/or $OCH_3$. Special special reference is made to the aminosilicones sold by Wacker Corporation under the trade name Belsil ADM 652 and Belsil ADM 653.

(2) silicone graft copolymer comprising an organopolysiloxane segment as a main chain thereof and an unsaturated monomer-derived polymer segment as a side chain thereof, which is obtainable by firstly reacting an aminopropyl dimethicone with the thiolactone of acetyl homocysteine and then graft copolymerizing the thus obtained mercapto modified dimethicone with a mixture of N,N-dimethylacrylamide and N-t-butylacrylamide. Such a polymer is known under the CTFA name Polysilicone 28 and marketed by Kao Corporation.

(3) an organopolysiloxane, wherein at least two silicon atoms in an organopolysiloxane segments constituting a main chain of the organopolysiloxane are bound to poly(N-acylalkyleneimine) segments consisting of repeating units represented by the following general formula via alkylene group containing hetero atom:

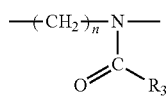

wherein $R^3$ is a hydrogen atom, an alkyl group having 1 to 22 carbon atoms, an aralkyl group, or an aryl group; and n is 2 or 3; wherein the number-average molecular weight of the poly(N-acylalkyleneimine) segment is from 1,200 to 5,500, wherein the mass ratio of the organopolysiloxane segments (a) constituting the main chain to the poly(Nacylalkyleneimine) segments (b) i.e., a/b is from 35/65 to 60/40, wherein the weight-average molecular weight of the adjacent poly(N-acylalkyleneimine) segments is from 1,300 to 5,500, and wherein the weight-average molecular weight of the organopolysiloxane segment constituting the main chain is from 7,000 to 100,000. Such a polymer is known under the CTFA name Polysilicone 9 and marketed by Kao Corporation. Derivatives of this polymer are disclosed in EP2502615 which is referenced herein.

The total concentration of silicone compounds is in the range from 0.1% to 5% by weight, preferably from 0.2% to 4% by weight, and more preferably from 0.25% to 2.5% by weight, calculated to the total of the composition.

Optimal effects are observed when the weight ratio of aminated silicones to total cationic polymer is in the range of 10:1 to 1:1.

The composition is an aqueous composition with water content of more than 60%, preferably 80 to 95%, more preferably 82 to 92% by weight, calculated to the total of the composition, and which may comprise organic solvents with a concentration of up to 10% by weight, calculated to the total of the composition. The organic solvents are selected from $C_1$ to $C_4$ linear or $C_3$ to $C_4$ branched alcohols or aromatic alcohols. Suitable $C_1$ to $C_4$ linear alcohols are ethanol, n-propanol, and n-butanol, glycerol, propylene glycol, butylene glycol and suitable $C_3$ to $C_4$ branched alcohols are iso-propanol, tert-butanol, iso-butanol. Aromatic alcohols are for example phenol, phenoxyethanol, benzyl alcohol, 2-phenylethanol, 2-benzoyloxyethanol. The skilled in the art will recognize that some of the aforementioned organic solvents can act as preservatives.

The composition may further comprise conditioning polymers with charge densities in the range of 0.001 meq/g to 2 meq/g. Suitable polymers are based on cationic cellulose and are known under their CTFA names Polyquaternium 10 and Polyquaternium 67. Further suitable are polymers based on cationized guar gums as they are marketed under the trade name Jaguar by Rhodia Corporation.

The composition may further comprise one or more ceramide compound, such as the one according to general formula:

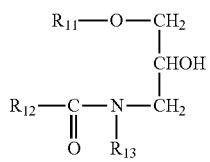

where $R^{11}$ and $R^{12}$ are independent from each other alkyl- or. alkenyl group with 10 to 22 carbon atoms, $R^{13}$ is alkyl or hydroxyl alkyl with 1 to 4 carbon atoms group and n is a number between 1 to 6, preferably 2 or 3. The preferred compound according to the above chemical structure is cetyl-PG-hydroxyethylpalmitamide. Concentration of ceramide type of compounds ranges from 0.01% to 2%, preferably 0.01% to 1% by weight calculated to the total of the composition.

The composition may further comprise ubiquinone of the formula

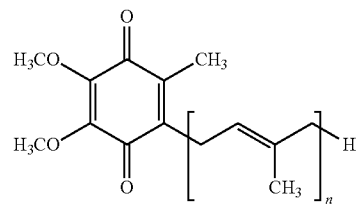

wherein n is a number from 1 to 10. The concentration of ubiquinone can vary between 0.001% and 10% by weight, calculated to the total of the composition.

The composition may further comprise one or more amino acids, preferably at a concentration in the range of 0.01% to 5%, preferably 0.1% to 3% and more preferably 0.2% to 2.5% and most preferably 0.25% to 2% by weight calculated to the total of the composition. Suitable ones are all of the known amino acids such as, arginine, alanine, asparagine, glutamine, glycine, histidine, leucine, lysine, methionine, phenylalanine, proline, serine, threonine, tryptophan, tyrosine and valine.

The composition may comprise vitamins and/or their derivatives such as vitamins A, B group, C, D group, E group, and K. It may further comprise antioxidants such as green tea extract, emblica extract, rosemary extract, and *ginkgo* extract.

The composition may further comprise proteins or hydrolyzed proteins such as keratin, elastin, collagen, or the ones generated from wheat, barley, quinoa, rye, rice, milk, amaranth, hazelnut, corn, soybean, avocado, brazil nut, casein, cottonseed, egg, honey, jojoba, oat, potato, royal jelly, sesame, silk, sweet almond, whey, and yeast. Proteins or protein hydrolyzates are comprised at a concentration in the range from 0.01% to 5%, preferably 0.1% to 3% and more preferably 0.2% to 2.5% and most preferably 0.25% to 2% by weight calculated to the total of the composition.

In another embodiment of the present invention the composition comprise one or more hair direct dyes. Suitable ones are cationic, anionic and nitro dyes. Plant dyes are also suitable for the compositions of the present invention.

Suitable anionic direct dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium. Among those, the most preferred anionic dyestuffs are Acid Red 52, DC Violet 2, DC Red 33, DC Orange 4, DC Red 27, DC Yellow 10, HC Blue 18, HC Red 18, and HC Yellow 16.

Suitable cationic dyes are in principle those available on the market for cosmetic hair colouring applications. For this purpose, special reference is made to the PCT application WO 95/15144 of Ciba-Geigy AG. Some examples to those are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic red 51, Basic Yellow 87, HC Blue 17 and Basic Orange 31. The most preferred ones are Basic red 51, Basic Yellow 87 and Basic Orange 31 sold by BASF, and HC Blue 17.

Suitable nitro dyes are HC Blue No. 2, HC Blue No. 4, HC Blue No. 5, HC BOlue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs can also be used alone or in combination with synthetic direct-acting dyestuffs, for example henna (red or black), alkanna root, laccaic acid, indigo, logwood powder, madder root and rhubarb powder.

The composition may comprise one or more hair direct dye at a total concentration of 0.01% to 10%, preferably 0.05% to 7.5% and more preferably 0.1% to 5% by weight calculated to the total of the composition. The composition can also comprise a mixture of several direct dyes, i.e., an anionic, a cationic and/or nonionic ones. In such a case the dyes may be mixed at any ratio with each other.

The composition may comprise oils from vegetable origin. Vegetable $C_{10}$- to $C_{35}$-fatty acid triglycerides are for example castor oil, coconut oil, corn oil, cottonseed oil, olive oil, palm kernel oil, peanut oil, rapeseed oil, sunflower oil, safflower oil, sesame oil, soybean oil, almond oil, cashew oil, hazelnut oil, jojoba oil, macadamia oil, pecan oil, pine nut oil, pistachio oil, walnut oil, grapefruit seed oil, lemon oil, orange oil, pumpkin seed oil, flaxseed oil, apricot kernel oil, argan oil, avocado oil, babassu oil, cocoa butter, grape seed oil, mustard oil, poppyseed oil, prune kernel oil, rice bran oil, and what germ oil.

The composition may comprise fatty alcohols are the ones with a carbon chain length of 14 to 22 C atoms which may be saturated or unsaturated, linear or branched which may as well be substituted. Non-limiting examples are myristyl alcohol, cetyl alcohol, stearyl alcohol, behenyl alcohol and cetostearyl alcohol, oleyl alcohol, as well as their mixtures.

The composition may comprise waxes which are esters of fatty acids with fatty alcohols wherein at least one of the fatty components of the ester has a carbon chain length from $C_{10}$ to $C_{22}$. Suitable waxes are beeswax, lanolin, carnauba wax, candelilla wax, ouricury wax, cetyl palmitate, isopropyl plamitate, octyl palmitate, isocetyl palmitate, and octyl stearate, myristyl myristate, lauryl palmitate, as well as their mixtures. Further suitable waxes are diesters of adipic acid with mixed diesters of caprylic, capric, hydroxystearic, and isostearic acid which are available under the CTFA names bis-diglyceryl polyacyladipate-1 and bis-diglyceryl polyacyladipate-2, as well as their mixtures. The preferred waxes are bis-diglyceryl polyacyladipate-1 and bis-diglyceryl polyacyladipate-2.

The composition may comprise petrolatum-based products are linear and/or branched paraffins with a carbon chain length of $C_6$ to $C_{12}$, mineral oils, preferably light mineral oils, and petroleum jelly, as well as their mixtures.

The total concentration of oil from vegetable or animal origin, fatty alcohols and waxes as well as petrolatum-based products is limited to a maximum of 5% by weight, calculated to the total of the composition. The skilled in the art will recognize that the composition does not comprise surfactants and therefore the miscibility of hydrophobic substances is limited. However, the skilled in the art will select an appropriately low concentration of aforementioned hydrophobic substances to maintain a unified composition.

The aqueous composition of the present invention may further comprise one or more UV filters which may be selected from water soluble ones as well as oils soluble ones. The oil soluble UV filter are more preferred ones as they show no interaction with the cationic quaternary ammonium polymers. Non-limiting examples are 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2.4-dihydroxybenzophenone, 2.2'.4.4'-tetrahydroxy-benzophenone, 2-hydroxy-4-methoxybenzophenone and its 5-sulfonic acid or the sodium salt thereof, 2.2'-dihydroxy-4.4'-dimethoxybenzophenone, 2-hydroxy-5-chlorobenzophenone, 2.2'-dihydroxy-4-methoxybenzophenone, 2.2'-dihydroxy-4.4'-dimethoxy-5.5'-disulfobenzo-phenone or the sodium salt thereof, 2-hydroxy-4-octyloxybenzophenone, 2-hydroxy-4-methoxy-4'-methylbenzophenone, 3-benzyl-idenecampher, 3-(4'-sulfo)-benzyl-idenebornane-2-one and the salts thereof, 3-(4'-methyl benzylidene)-DL-campher, and/or polysilicone-15.

The total UV filter concentration may be in the range of 0.01% to 1% by weight, calculated to the total of the composition.

The composition may comprise essential oils such as angelica essential oil, anise essential oil, basil essential oil, bergamot essential oil, bitter almond essential oil, black pepper essential oil, boldo essential oil, calamus essential oil, camomile essential oil, cardamom essential oil, carrot seed essential oil, cassia essential oil, cedarwood essential oil, cinnamon essential oil, citronella essential oil, coriander essential oil, cypress essential oil, dill essential oil, eucalyptus essential oil, fennel essential oil, frankinscense essential oil, geranium essential oil, ginger essential oil, grapefruit essential oil, helicrysum essential oil, jasmine essential oil, juniper essential oil, lavandin essential oil, lavender essential oil, lemon essential oil, lemongrass essential oil, lime essential oil, mandarin essential oil, melissa essential oil, mullein essential oil, myrtle essential oil, orange essential oil, oregano essential oil, peppermint essential oil, pine essential oil, rose essential oil, rosemary essential oil, rosewood essential oil, sandalwood essential oil, spearmint essential oil, tangerine essential oil, tea tree essential oil, thuja essential oil, vanilla essential oil, wintergreen essential oil, ylang ylang essential oil. The skilled in the art will recognize that some of the aforementioned essential oils can be employed as fragrance. However, the composition of the present invention may comprise a conventional fragrance as well.

The total concentration of essential oils is less than 1% by weight, calculated to the total of the composition. The skilled in the art will recognize that the composition does not comprise surfactants and select a concentration sufficiently low to maintain a unified composition.

The composition of the present invention may further comprise natural plant extracts. Within the meaning of the present invention the extracts are liquid extracts and prepared by mixing plant parts such as leaves, fruits, blossoms and roots with a solvent such as water, alcohol, propyleneglycol or mixture of more than one solvent and incubating for certain period of time and filtrating the undissolved plant parts. Suitable aqueous (e.g. steam-distilled) alcoholic or hydro-alcoholic plant extracts known per se are in particular aloe, pineapple, artichoke, arnica, avocado, valerian, bamboo, henbane, birch, stinging nettle, echinacea, ivy, wild angelica, gentian, ferns, pine needles, silver weed, *ginseng*, broom, oat, rose hip, hamamelis, hay flowers, elderberry, hop, coltsfoot, currants, chamomile, carrots, chestnuts, clover, burr root, cocoanut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc. Suitable trade products are, for example, the various "Extrapon" products, "HerbasolR", "SedaplantR" and "HexaplantR". Extracts and the preparation thereof are also described in "Hagers Handbuch der pharmazeutischen Praxis", 4th Ed.

Preferred plant extracts are prepared from *Vitis vinifera*, *Malus domestica*, *Camelia sinensis*, *Juglans regia* Ribes Uva-Crispa, *Ribes nigrum*, *Ribes rubrum* and *Punica granatum*. The above mentioned extracts may also be available in the powder form and such are also suitable within the meaning of the present invention.

The natural plant extracts are included into the compositions at a concentration of 0.001 to 1.0%, preferably 0.005 to 0.75%, more preferably 0.01 to 0.6% and most preferably 0.05 to 0.5% by weight, calculated to the total of the composition based on dry matter of the extract.

The composition may further comprise fragrance and any commonly known preservatives.

The aqueous composition of the present invention can be applied onto hair by all known physical means such as 1) spraying the composition with atomization by aerosol or non-aerosol means, 2) foaming the composition either with propellant or with a squeeze or pump foamer without the use of propellants, 3) spreading the composition onto a woven or non-woven substrate wherein the hair is contacted with the substrate, 4) directly immersing the hair with the composition.

The application of the composition onto hair may take place before or after washing or rinsing the hair. Upon treating the hair with the composition, the hair can be dried by elevating the temperature of the hair with all known means. Preferred is the application of temperatures in the range from 40° C. to 90° C., particularly preferred by operating a hair dryer in that temperature range.

The following examples are to illustrate the invention, but not to limit it.

EXAMPLES

The following composition was prepared by conventional dissolution and mixing techniques.

|  | Example 1 | Example 2 | Example 3 | Example 4 | Example 5 | Example 6 | Example 7 | Example 8 |
|---|---|---|---|---|---|---|---|---|
| Polyquaternium 16 (3.3 meq/g) | 1.5 | — | — | 0.5 | — | — | 1.5 | — |
| Polyquaternium 7 (3.1 meq/g) | — | 1.5 | — | 0.5 | — | — | — | — |
| Polyquaternium 37 (2.3 meq/g) | — | — | 1.5 | 0.5 | 1.5 | — | — | — |
| Polyacrylamidopropyltrimonium chloride (4.8 meq/g) | 0.5 | — | — | 0.2 | 0.7 | — | — | 0.5 |

-continued

|  | Example 1 | Example 2 | Example 3 | Example 4 | Example 5 | Example 6 | Example 7 | Example 8 |
|---|---|---|---|---|---|---|---|---|
| Polyquaternium 16 (6.1 meq/g) | — | 0.5 | — | 0.2 | — | — | — | — |
| Polyquaternium 22 (6.2 meq/g) | — | — | 0.5 | 0.2 | — | — | — | — |
| Amodimethicone | 0.5 | 0.5 | 0.5 | 0.5 | 0.5 | 0.5 | 0.5 | 0.5 |
| Fragrance | 0.2 | 0.2 | 0.2 | 0.2 | 0.2 | 0.2 | 0.2 | 0.2 |
| Ethanol | 5 | 5 | 5 | 5 | | 10 | 5 | 5 |
| Isopropanol | — | — | — | 5 | 10 | — | — | — |
| Preservatives | 1 | 1 | 1 | 1 | 1 | 1 | 1 | 1 |
| Water | | | | Ad 100 g | | | | |

Human hair streaks (20 cm long, Caucasian hair) were purchased from International Hair Products Inc., Glendale, N.Y., USA. Each hair streak was weighed in its dry state. The compositions 1, and 6-8 were applied on separate hair streaks by spraying about 2 g of the composition onto the hair and the resulting wet weight of the hair streak was recorded. A blow dryer was mounted in a predefined distance to the hair streaks and set to 60° C. The weight of the hair streaks was recorded every 30 s and cumulative water loss was calculated according to the following equation:

$$\text{Water Loss [\%]} = \sum_{i=30s}^{600s} \frac{\text{Wet Weight [g]} - \text{Weight Process Step}_i \text{ [g]}}{\text{Wet Weight [g]} - \text{Dry Weight [g]}} \cdot 100\%$$

| | Water loss [%] | | | |
|---|---|---|---|---|
| Time Point [s] | Example 6 (comparative) | Example 7 (comparative) | Example 8 (comparative) | Example 1 (inventive) |
| 30 | 8 | 9 | 13 | 24 |
| 60 | 15 | 16 | 24 | 41 |
| 90 | 24 | 26 | 39 | 57 |
| 120 | 31 | 33 | 50 | 65 |
| 150 | 38 | 42 | 59 | 74 |
| 180 | 44 | 55 | 66 | 80 |
| 210 | 52 | 60 | 75 | 84 |
| 240 | 58 | 68 | 81 | 89 |
| 270 | 63 | 86 | 87 | 93 |
| 300 | 71 | 91 | 90 | 95 |
| 330 | 75 | 94 | 91 | 100 |
| 360 | 80 | 96 | 96 | 100 |
| 390 | 84 | 100 | 100 | 100 |
| 420 | 89 | 100 | 100 | 100 |
| 450 | 93 | 100 | 100 | 100 |
| 480 | 96 | 100 | 100 | 100 |
| 510 | 98 | 100 | 100 | 100 |
| 540 | 100 | 100 | 100 | 100 |
| 570 | 100 | 100 | 100 | 100 |
| 600 | 100 | 100 | 100 | 100 |

As evident from the presented data above, the composition comprising both the PQ-16 and polyacrylamidopropyltrimonium chloride led to much shorter drying times of human hair compared to compositions comprising the individual polymers or no polymers at all. An 80% water loss was achieved at 180 s with the inventive composition, whereas for the closest comparative composition it took 240 s to reach this level of water loss.

What is claimed is:

1. An aqueous cosmetic composition for keratin fibers, comprising:
    (a) two or more cationic polymers and/or their salts comprising:
        (a)(i) a first cationic polymer having a charge density in the range of 2 meq/g to 4 meq/g; and
        (a)(ii) a second cationic polymer having a charge density in the range of 4.1 meq/g to 7 meq/g;
    (b) amodimethicone present at a concentration range from 0.1% to 5% by weight, calculated to a total of the aqueous cosmetic composition; and
    (c) from 80% to 95% by weight of water calculated to a total of the aqueous cosmetic composition,
    wherein the first cationic polymer is present at a concentration range from 0.1% to 5% by weight, calculated to the total of the aqueous cosmetic composition, and is at least one selected from:
    Polyquaternium 16 and/or its salts having a cationic charge density of 2 meq/g to 4 meq/g;
    Polyquaternium 7 and/or its salts; and
    Polyquaternium 37 and/or its salts having a cationic charge density of 2 meq/g to 4 meq/g,
    wherein the second cationic polymer is present at a concentration range from 0.01% to 5% by weight, calculated to the total of the aqueous cosmetic composition, and is at least one selected from:
    Polyquaternium 22 and/or its salts;
    Polyquaternium 16 and/or its salts having a cationic charge density of 4.1 meq/g to 7 meq/g;
    Polyacrylamidopropyltrimonium chloride; and
    Polyquaternium 37 and/or its salts having a cationic charge density of 4.1 meq/g to 7 meq/g, and
    further wherein a weight ratio of the first cationic polymer to the second cationic polymer ranges from 5:1 to 1:1.

2. The aqueous cosmetic composition according to claim 1, wherein the second cationic polymer is polyacrylamidopropyltrimonium chloride.

3. The aqueous cosmetic composition according to claim 1, wherein the first cationic polymer is Polyquaternium 16.

4. The aqueous cosmetic composition according to claim 1, further comprising:
    one or more ingredients selected from the group consisting of fragrances, preservatives, antioxidants, essential oils, vegetable oils, organic solvents, ceramides, ubiquinones, UV filtering compounds, amino acids, vitamins, and plant extracts.

5. The aqueous cosmetic composition according to claim 1, further comprising:
    a hair direct dye.

6. A method for reducing the drying time of hair, the method comprising:
    applying the aqueous cosmetic composition according to claim 1 onto hair;
    washing the hair having the aqueous cosmetic composition applied thereto; and
    drying the hair with a hair drier.

7. The method according to claim 6, wherein the hair drier is operable at temperatures from 40° C. to 90° C.

8. A kit comprising:
   the aqueous cosmetic composition according to claim 1, wherein the components (a)(i), (a)(ii), and (b) are provided together as one component of the kit or separate as separate components of the kit; and
   at least one blow drier.

9. The aqueous cosmetic composition according to claim 1, wherein the weight ratio of the first cationic polymer to the second cationic polymer ranges from 3:1 to 1:1.

* * * * *